US011565063B1

(12) United States Patent
Chin et al.

(10) Patent No.: US 11,565,063 B1
(45) Date of Patent: Jan. 31, 2023

(54) SPEAKING ENDOTRACHEAL TUBE AND METHOD OF USE

(71) Applicants: Albert K Chin, Palo Alto, CA (US); Dan M Meyer, Dallas, TX (US)

(72) Inventors: Albert K Chin, Palo Alto, CA (US); Dan M Meyer, Dallas, TX (US)

( * ) Notice: Subject to any disclaimer, the term of this patent is extended or adjusted under 35 U.S.C. 154(b) by 0 days.

(21) Appl. No.: 17/460,222

(22) Filed: Aug. 29, 2021

(51) Int. Cl.
*A61M 16/04* (2006.01)

(52) U.S. Cl.
CPC .... *A61M 16/0445* (2014.02); *A61M 16/0402* (2014.02); *A61M 16/0463* (2013.01); *A61M 16/0486* (2014.02); *A61M 2210/065* (2013.01)

(58) Field of Classification Search
CPC .............. A61M 16/04–0486; A61M 2210/065
See application file for complete search history.

(56) References Cited

U.S. PATENT DOCUMENTS

| 4,593,689 | A | * | 6/1986 | White ................. A61F 2/20 128/201.19 |
| 5,702,365 | A | | 12/1997 | King |
| 10,820,861 | B2 | | 11/2020 | Chaudhry |
| 2008/0110468 | A1 | * | 5/2008 | Nelson .............. A61M 16/0486 128/207.15 |
| 2011/0190596 | A1 | | 8/2011 | Hacker et al. |
| 2013/0098358 | A1 | | 4/2013 | Blom et al. |
| 2014/0238398 | A1 | * | 8/2014 | Christopher ...... A61M 16/0816 128/204.22 |
| 2015/0007826 | A1 | | 1/2015 | Chaudhry |
| 2016/0001110 | A1 | * | 1/2016 | Hamilton ............... A62B 18/08 381/385 |
| 2018/0369527 | A1 | * | 12/2018 | Arlinghaus, Jr. . A61M 16/0816 |

* cited by examiner

*Primary Examiner* — Rachel T Sippel

(57) ABSTRACT

An endotracheal tube is disclosed that allows a patient to speak while intubated. The endotracheal tube includes a balloon for seating against the trachea and a collapsible portion proximal to the balloon that aligns with the vocal cords. The collapsible portion may be held open by an inner tube which translates within the endotracheal tube. Suction and balloon inflation conduits span the collapsible portion so that suction and balloon inflation may be performed while the patient is speaking. A small distal tube that bypasses the balloon provides some airflow while the patient speaks.

14 Claims, 9 Drawing Sheets

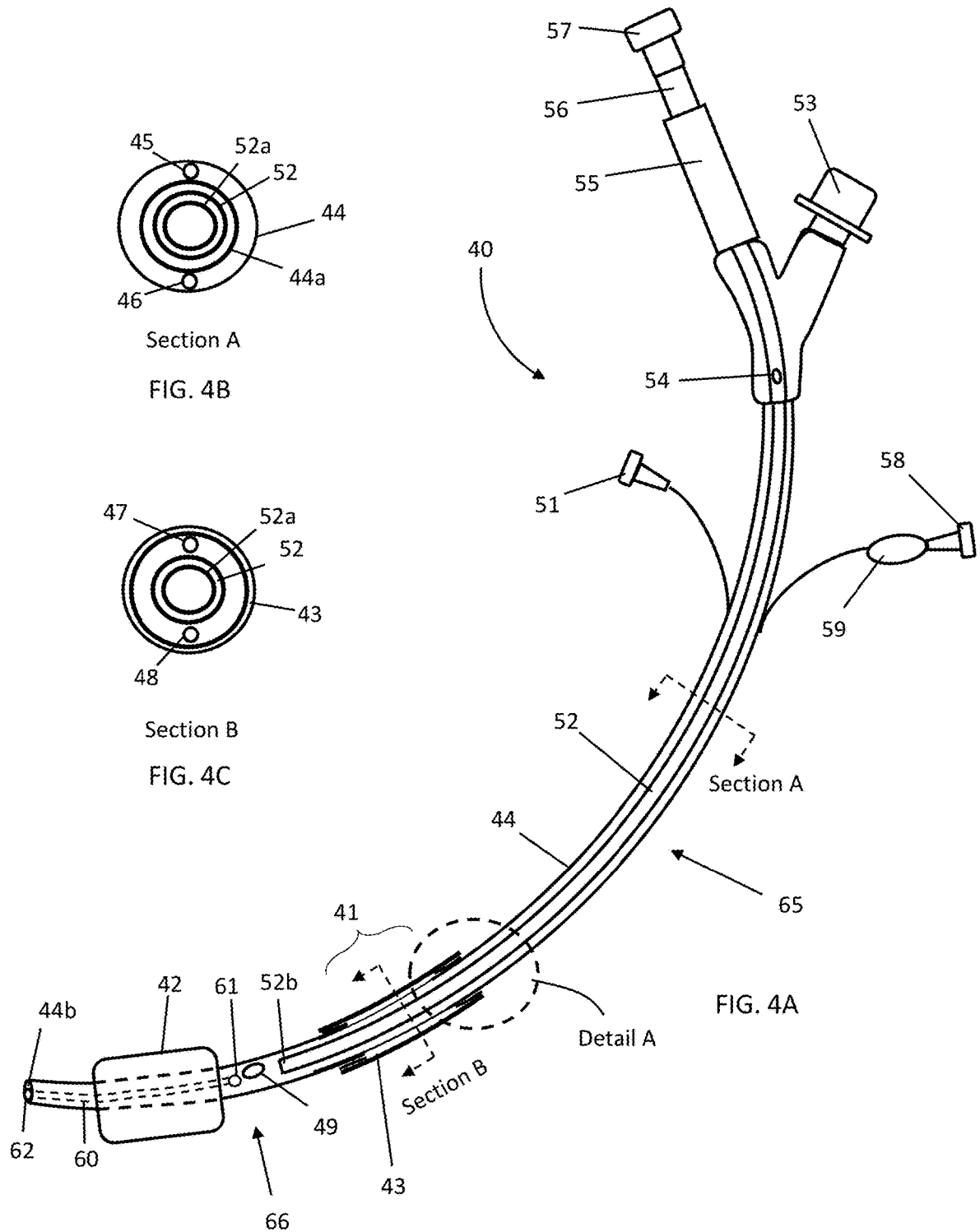

Detail A

Section B

Section B

SPEAKING ENDOTRACHEAL TUBE AND METHOD OF USE

TECHNICAL FIELD

This disclosure relates generally to devices and methods to allow patients with an indwelling endotracheal tube to speak. More specifically, it relates to an endotracheal tube that allows movement of the vocal cords for speech production.

BACKGROUND

Patients who require mechanical ventilation for respiratory failure undergo placement of an endotracheal tube, a flexible, polymeric curved tube with an outer diameter of approximately 10 mm to 13 mm for adult subjects. The proximal end of the endotracheal tube extends out of the mouth of the patient for attachment to the ventilator machine, while the distal end of the endotracheal tube resides in the distal trachea. A soft balloon on the distal portion of the tube is inflated to seal the distal trachea to allow pressurized ventilatory assistance to occur while avoiding aspiration of fluid and foreign material into the lung during the mechanical ventilation process. As the large diameter endotracheal tube passes through the trachea of the patient, it markedly displaces the vocal cords, preventing normal speech. There are 2 million intensive care unit intubations performed each year in the United States, and with the current respiratory viral pandemic, mechanical ventilation may be required for multiple weeks at a time. Communication between the patients and their health care providers becomes difficult and frustrating for an extended time, and it is desirable to utilize an endotracheal tube that enables the patient to speak for short periods of time.

SUMMARY

The present disclosure is directed to endotracheal tubes that are adapted to allow speaking. In some embodiments, an endotracheal tube system includes an elongate tube having a central lumen, a suction lumen, and a balloon inflation lumen and a collapsible section disposed toward the distal end of the tube that is capable of substantially flattening under the force of vocal cords. The endotracheal tube may have as an inflatable balloon disposed on the elongate tube distal to the collapsible section and in fluid communication with the balloon inflation lumen.

In some embodiments, the collapsible section includes a flexible tube, that spans between a proximal section of the elongate tube and a distal section of the elongate tube, and at least one substantially non-collapsible tube for providing fluid communication across the collapsible section.

In some embodiments the inner tube is slidably disposed inside of the central lumen and has a radial stiffness sufficient to resist collapsing due to the force of vocal cords.

The endotracheal tube system may include a balloon bypass lumen which provides fluid communication between the portion of the trachea distal to the balloon and the portion of the trachea proximal to the balloon. The balloon bypass lumen may include an outlet proximal to the balloon that is capable of being closed when a patient is not speaking; in some embodiments an inner tube slidably disposed inside of the central lumen that is capable of blocking the balloon bypass lumen to prevent air flow therethrough.

In some embodiments illustrated in the present disclosure, a speaking endotracheal tube includes a tubular body configured to be placed in a trachea of a patient and an inner tube slidably located in the lumen of the tubular body that is capable of transmitting gas between the trachea and a ventilator fitting on the endotracheal tube. The inner tube may have an aperture near its proximal end for transmitting gas between its lumen and the lumen of the tubular body.

In some embodiments, the speaking endotracheal tube includes a collapsible section which aligns with the vocal cords while the endotracheal tube resides in the patient The collapsible section may have at least one substantially non-collapsible tube for providing fluid communication across the collapsible section.

In some embodiments, the non-collapsible tube is in fluid communication with either the suction lumen or the balloon inflation lumen.

In some embodiments, the speaking endotracheal tube includes a balloon bypass lumen capable of providing fluid communication between the portion of the trachea distal to the balloon and the portion of the trachea proximal to the balloon. The balloon bypass lumen may have an outlet proximal to the balloon that is capable of being closed when a patient is not speaking, and in some embodiments, the inner tube is capable of blocking the balloon bypass lumen to prevent air flow therethrough.

In an embodiment described herein, a method of operation for inserting a speaking endotracheal tube into a patient is disclosed. The method may include providing an elongate tube having a central lumen, a suction lumen, a balloon inflation lumen, and a collapsible section. An inner tube is slidably disposed in the lumen of the elongate tube and an inflatable balloon is disposed on the elongate tube distal to the collapsible section and in fluid communication with the balloon inflation lumen.

In some embodiments, the method includes placing the endotracheal tube into the trachea of the patient. The method my further include, aligning the collapsible section with the vocal cords of the patient and inflating the balloon to secure the speaking endotracheal tube.

In some embodiments, the method includes the step of moving the distal end of the inner tube to a position proximal to the collapsible section to allow speaking. Additionally, the inner tube may be moved such that its distal end resides distal to the collapsible section so that the inner tube resists collapsing under a closing force of the vocal cords.

In some embodiments, the elongate tube may include a balloon bypass lumen providing fluid communication between the portion of the trachea distal to the balloon and the portion of the trachea proximal to the balloon. In some embodiments, the inner tube may be moved such that it blocks fluid communication of the balloon bypass lumen.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 4A illustrates a side partial cross-sectional view of an embodiment of a speaking endotracheal tube according to embodiments of the present disclosure.

FIG. 4B illustrates a cross-sectional view of the embodiment of FIG. 4A.

FIG. 4C illustrates a cross-sectional view of a collapsible portion of the embodiment of FIG. 4A.

DETAILED DESCRIPTION

Figure 1A:
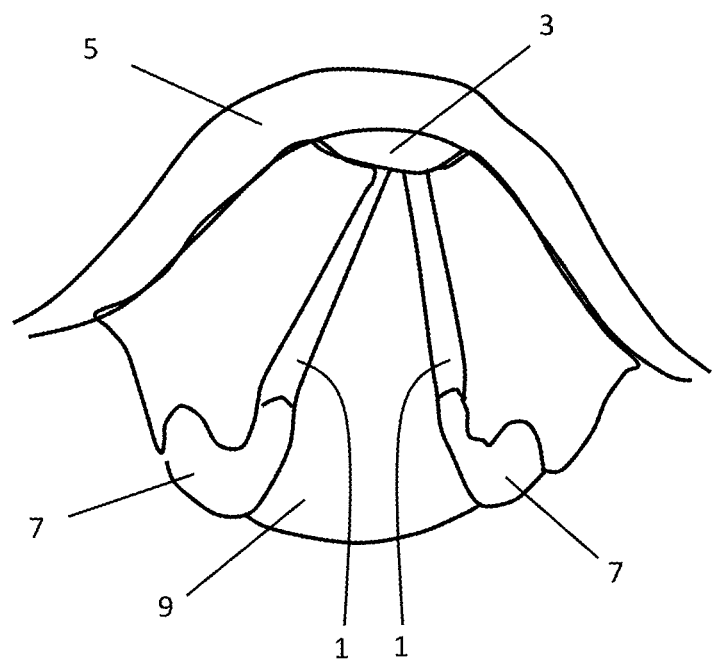
FIG. 1A illustrates the vocal cord anatomy in the open state.

A description of example embodiments follows.

Embodiments will now be described with reference to the accompanying drawings, which show some, but not all of the disclosed embodiments. While this invention has been particularly shown and described with references to example embodiments thereof, it will be understood by those skilled in the art that various changes in form and details may be made therein without departing from the scope of the invention encompassed by the appended claims. Furthermore, while several embodiments are described, the scope of the embodiments should not be construed to be limited to those set forth herein.

For the purposes of this disclosure, the term "proximal" and "distal" are used with reference to the device; that is, "proximal" denotes the region near the end of the device that connects to the ventilator machine and "distal" denotes region extending away from the ventilator machine towards the section that contains the balloon.

A speaking endotracheal tube consists of a tube with an outer diameter equal to the standard diameter of conventional endotracheal tubes throughout most of its length while having a thin-walled section at the location of the vocal cords. An inner tube is advanced distally within the lumen of the speaking endotracheal tube to dilate and stent the thin-walled section to the larger inner diameter of the remainder of the tube, allowing high flow patient ventilation to occur. When speech by the intubated patient is desired, the inner tube is retracted to allow collapse of the thin-walled section of the endotracheal tube, allowing nearly normal movement of the vocal cords for recognizable phonation. In some embodiments, thin-walled section of the endotracheal tube is formed of two small diameter inner stainless steel tubular struts covered by a thin-walled tubular membrane connected in an airtight fashion to the proximal and distal normal-sized portions of the endotracheal tube. The tubular struts may be diametrically opposed and rigidly bonded to the balloon inflation lumen and the suction lumen that are present in the wall of the endotracheal tube. In some embodiments, an additional short lumen inside the central lumen of the endotracheal tube extends from the distal tip of the endotracheal tube to a port immediately proximal to the balloon. This lumen enables air flow to occur proximal to the balloon as the patient exhales, producing speech. The proximal portion of the exhalation lumen connected to the port may be flexible, such that it may be collapsed and sealed when the inner tube is fully advanced during the non-speaking configuration of the endotracheal tube. The proximal end of the inner tube is pulled proximally to retract it and allow patient phonation. The proximal portion of the inner tube may be keyed to prevent its rotation relative to the endotracheal tube, as in some embodiments, both the endotracheal tube and the inner tube contain a matching gentle curvature. The body of the endotracheal tube may be constructed of a soft polymer such as polyvinyl chloride (PVC). The inner tube may be constructed of a polymer such as polytetrafluoroethylene (PTFE), giving it sufficient structural rigidity to stent the tubular membrane open when it is advanced distally. The thin-walled tubular membrane at the collapsible portion may be constructed of a polymer, such as an inelastic polymer such as polyethylene terephthalate (PET) and it may be 1 mil or less in wall thickness; in some embodiments, it may be constructed of an elastic polymer such as polyurethane.

Figure 1B:
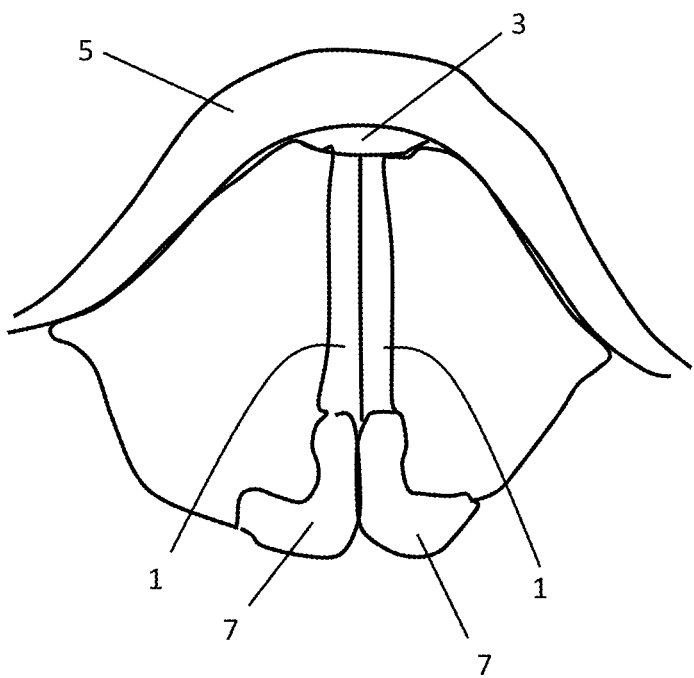
FIG. 1B illustrates the vocal cord anatomy in the closed, or speaking state.

FIGS. 1A and 1B illustrate a superior view of the vocal cord anatomy, in two different states for orientation purposes throughout this disclosure. The vocal cords 1 are supported anteriorly by the thyroid cartilage 3 and the epiglottis 5, and posteriorly, the vocal folds 1 are attached to the arytenoid cartilages 7. In FIG. 1A, the vocal cords 1 are depicted in an open position, and the tracheal lumen 9 can be seen through the opening. FIG. 1B shows the vocal cords 1 in a closed position, in apposition to allow phonation to occur. Vibration of the vocal cords upon exhalation produces intelligible speech.

Figure 2A:
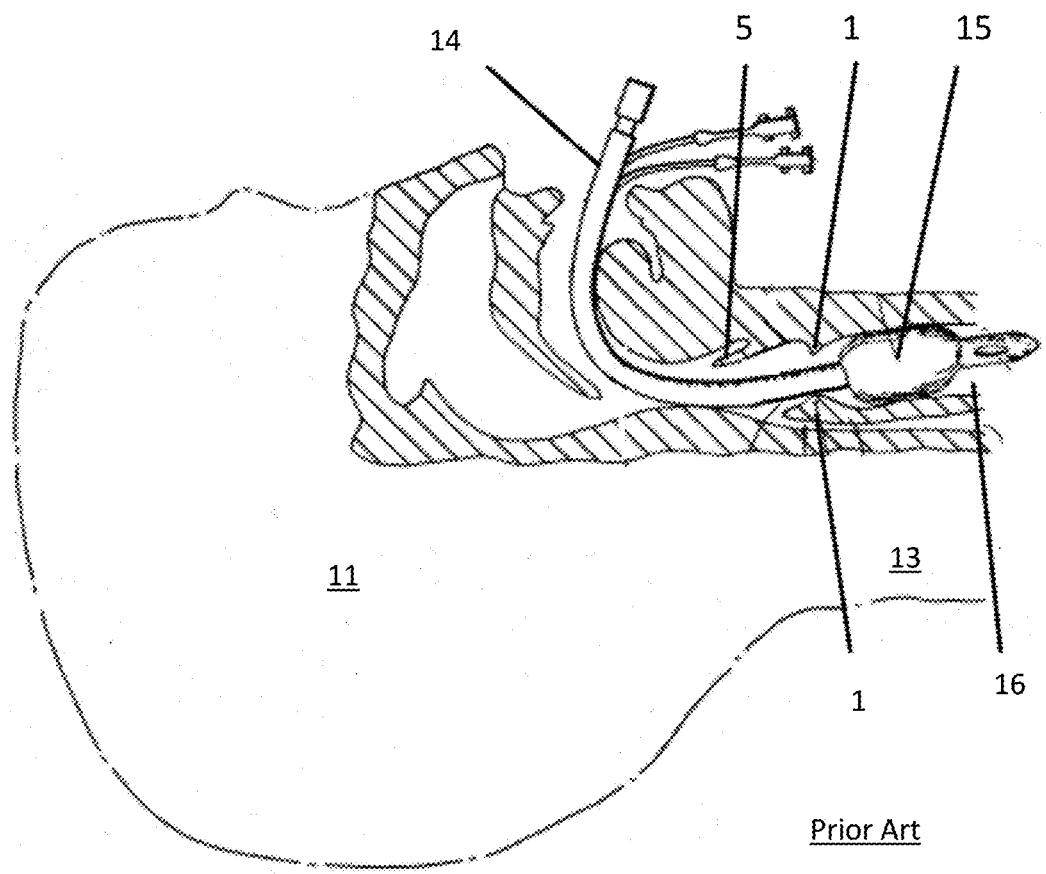
FIG. 2A illustrates a cross-sectional view of a patient with an endotracheal tube inserted.
Figure 2B:
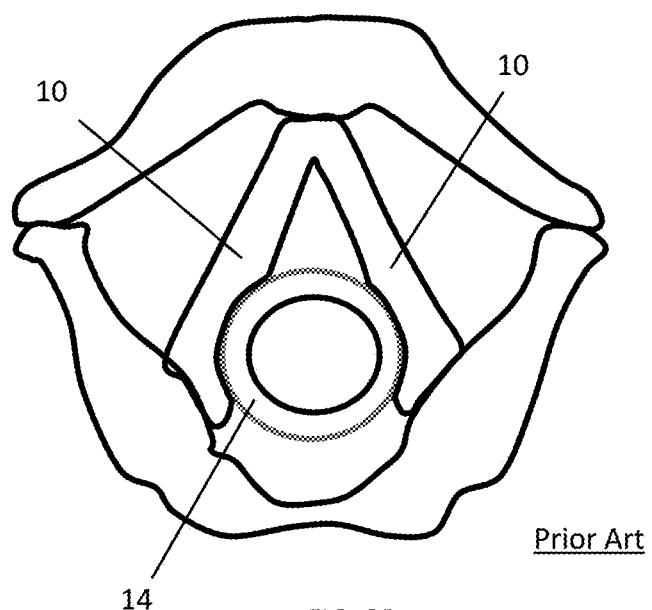
FIG. 2B illustrates a conventional endotracheal tube placed between the vocal cords.

FIG. 2A is a sagittal cross-section of a patient's head 11 and neck 13, showing an endotracheal tube 14 in position to provide mechanical ventilation. The epiglottis 5 and vocal cords 1 are shown for reference. A sealing balloon 15 near the distal end of endotracheal tube 14 is inflated in the patient's distal trachea 16 to seat against the trachea 16 to allow positive pressure airflow to expand the patient's lungs while preventing aspiration of mucous or other material into the lungs. FIG. 2B is a superior view of a transverse section at the level of the vocal cord, demonstrating that an emplaced endotracheal tube 14 stents the vocal cords 10 in an open position, preventing speech from occurring.

Figure 3:
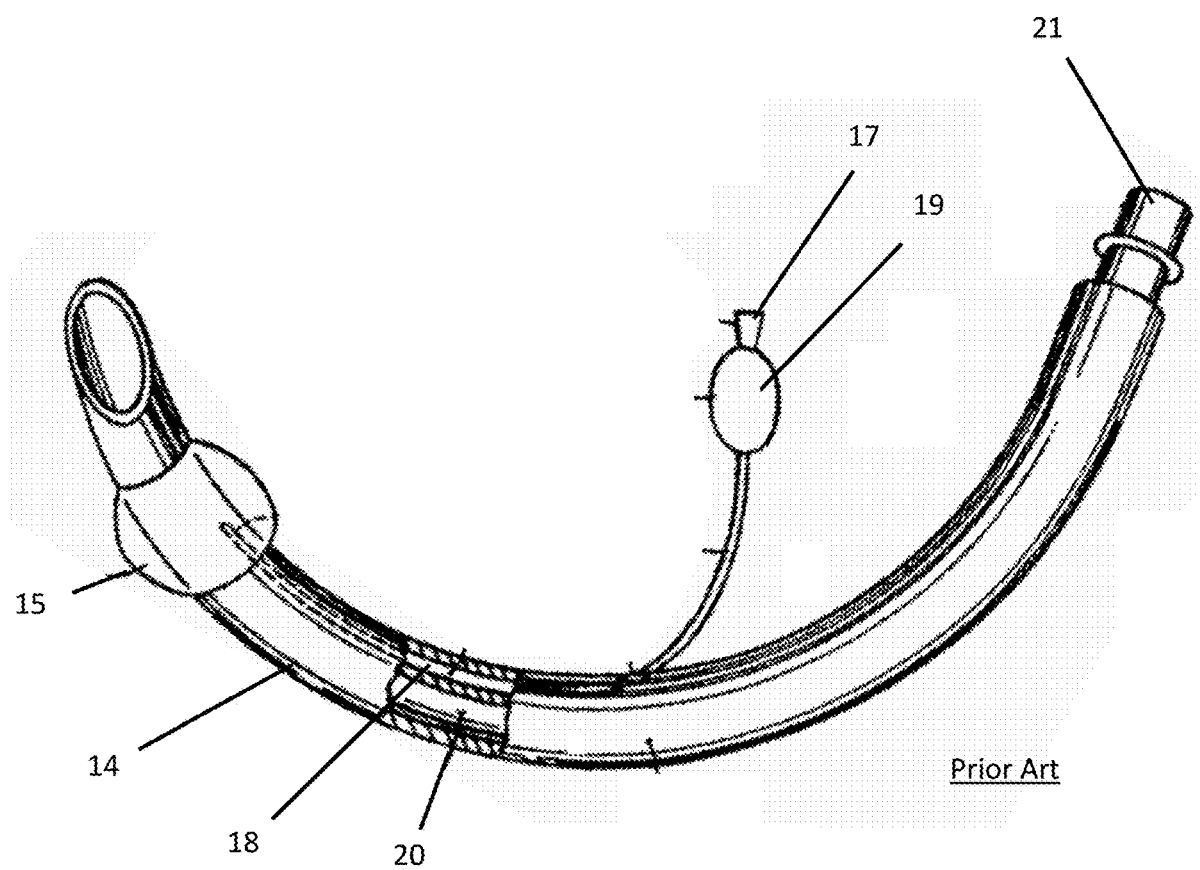
FIG. 3 illustrates the components of a conventional endotracheal tube.

Now with reference to FIG. 3, which illustrates a conventional endotracheal tube 14, containing a sealing balloon 15 near its distal end that is inflated via a luer lock check valve fitting 17 that allows the sealing balloon 15 to remain inflated after removal of the inflation syringe. The luer lock check valve fitting 17 is in fluid communication with balloon inflation lumen 18 which resides in the wall of the endotracheal tube 14, while a small flexible reservoir 19. also in fluid communication with the balloon inflation lumen 18.

allows the health care worker to gauge the pressure in the sealing balloon 15, ensuring adequate sealing of the mainstem bronchus without excessive pressurization. The balloon inflation lumen 18 is generally a small diameter lumen compared with the central lumen 20 that exits the distal end of the endotracheal tube 14. The central lumen 20 is used for patient ventilation, and it contains a proximal fitting 21 that connects to the ventilation tubing emanating from a mechanical ventilator. The average size of an endotracheal tube for adult males is size 8.0, indicating that the diameter of the central lumen 20 is equal to 8.0 mm.

FIG. 4A is a side section view (however, the balloon is not sectioned) of a speaking endotracheal tube 40 configured for high flow ventilation according to embodiments. The speaking endotracheal tube comprises a main tube 44 connected to a sealing balloon 42 near its distal end. The sealing balloon 42 is inflated via a pressure connector 58 (e.g., check valve), which is in fluid communication with a balloon inflation lumen 45 (FIG. 4B) which is colinear with the main tube 44; a small flexible reservoir 59 is also in fluid communication with the balloon inflation lumen 45, which allows the health care worker to gauge the pressure in the sealing balloon 42, ensuring adequate sealing of the mainstem bronchus without excessive pressurization. Section A, as illustrated in FIG. 4B, represents a sectional view through the main portion of the main tube 44. The main tube 44 has a large central lumen 44a, which may be approximately 8.0 mm in diameter for example, and two small lumens—a balloon inflation lumen 45 and a suction lumen 46, both of which may be approximately 1.5 mm in diameter, for example. The balloon inflation lumen 45 is used for inflation of the sealing balloon 42 and the suction lumen 46 is used for application of suction proximal to the sealing balloon 42 as described below. The central lumen 44a is used for patient ventilation and has, at its proximal end, a ventilation fitting 53 that connects to ventilation tubing emanating from a mechanical ventilator.

The suction lumen 46 ends in a suction lumen port 49 through the side of the main tube 44, allowing removal of mucous or debris residing in the mainstem bronchus proximal to sealing balloon 42. Balloon inflation is performed via injection of air using a syringe into pressure connector 58 on the proximal section of the main tube 44, while bronchial suctioning is performed via connection of a vacuum line to suction connector 51, which may be a luer fitting, for example.

Continuing with FIG. 4A, an inner tube 52 is disposed inside of the central lumen 44a of the main tube 44 and is capable of translating within the central lumen 44a. The speaking endotracheal tube 40 has enough column strength to be placed into a patient's trachea without binding, buckling, or bending excessively. The column strength may be provided by the inner tube 52, while the main tube 44 is relatively more flexible. Alternatively, both the inner tube 52 and main tube 44 may contribute to the column strength equally or in any other proportion. In some embodiments, the main tube 44 may have a collapsible portion with relatively low column strength, but the overall column strength of the speaking endotracheal tube may be accommodated by one or more other tubes or members that span the collapsible portion In some embodiments, the main tube 44 and the inner tube 52 may be pre-formed in the same curvature so that they are "keyed," that is, they do not rotate easily about their axis' relative to each other. In other embodiments, only the inner tube 52 is pre-formed in a curve, and the main tube 44 conforms to its curvature. In yet other embodiments, the main tube 44 may be pre-formed in a curve, and the inner tube 52 conforms to its shape. The inner tube 52 has adequate radial stiffness to withstand the closing of the vocal cords without collapsing. The inner tube 52 may be pre-curved to fit within the main tube 44, which also may be pre-curved to a similar extent.

Section A, as shown in FIG. 4B illustrates the location of the inner tube 52 inside of the central lumen 44a of the main tube 44 in an embodiment; the inner tube lumen 52a provides fluid communication between the distal and proximal ends of the speaking endotracheal tube 40. The speaking endotracheal tube 40 is connected to ventilator machine tubing via a ventilation fitting 53. In some embodiments, an inner tube port 54 through the sidewall of inner tube 52 provides fluid communication between a ventilator and the inner tube lumen 52a. In other embodiments, the inner tube lumen 52a may be in direct fluid communication with a ventilation fitting without a port. The inner tube 52 is open to the central lumen 44a at the distal end 52b of the inner tube 52. Distal to that portion, the central lumen 44a is in fluid communication with the trachea at the main tube distal end 44b providing an opening for air exchange with the patient (except when in the speaking configuration, as explained below). This arrangement provides an air pathway between the patient's trachea and the ventilation fitting 53 through the inner tube 52, regardless of the location of the inner tube 52, as it translates within the main tube 44. A radial gap may exist between the inner tube 52 and the central lumen 44a to allow translation of the inner tube 52 within the main tube 44; this gap may provide an air flow path between the inner tube 52 and the central lumen 44a, but the majority of the flow will travel through the inner tube lumen 52a if the gap is small.

The speaking endotracheal tube 40 includes a collapsible portion 41 proximal to the sealing balloon 42. In some embodiments, the collapsible portion 41 may reside 1-4 cm centimeters proximal to the sealing balloon 42, and the collapsible portion may be approximately 2 cm in length. The main tube 44 has a proximal section 65, and a distal section 66 connected by the collapsible portion 41; the collapsible portion is bridged by a collapsible tube 43 that has a thin wall.

Figure 4D:
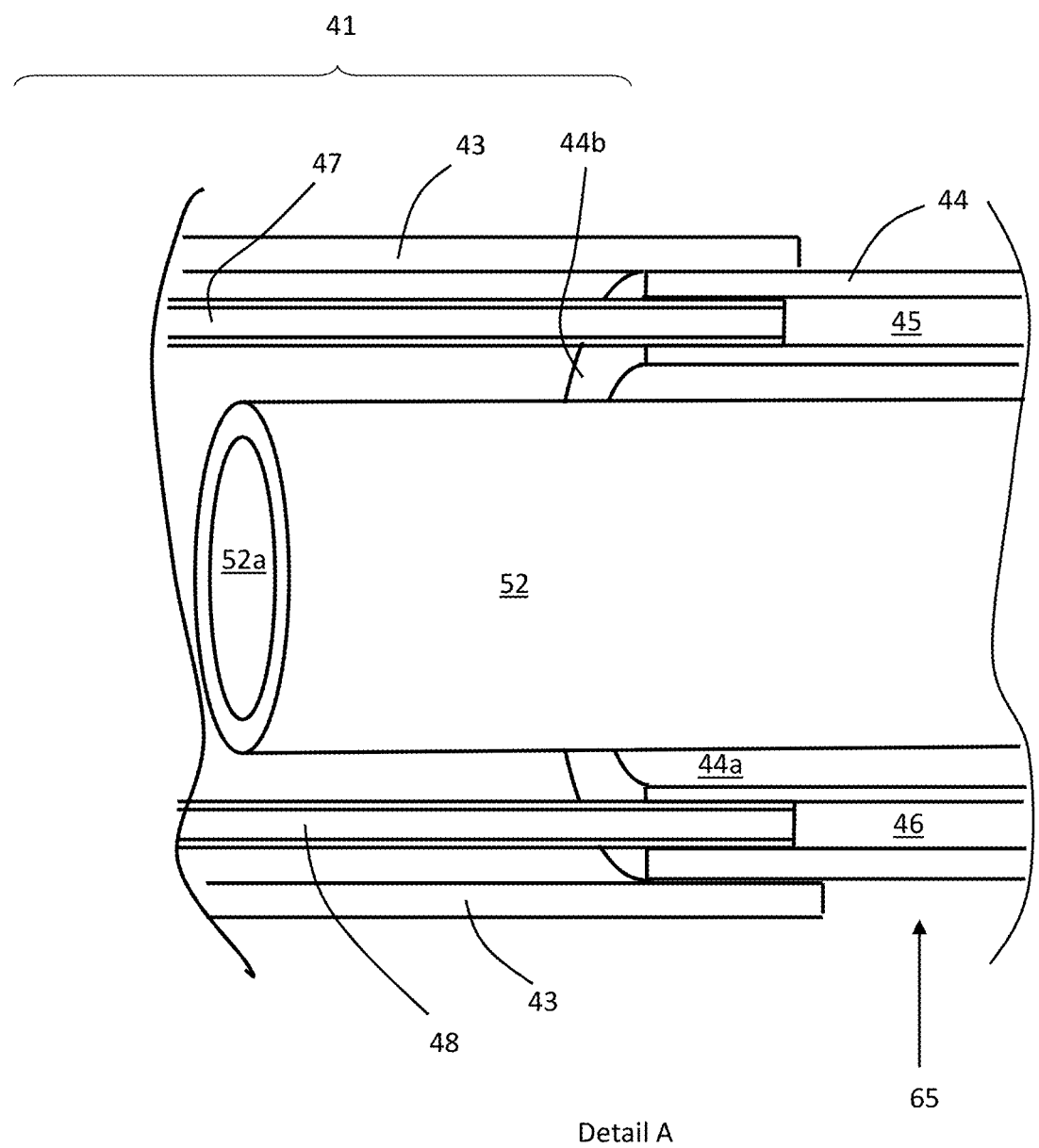
FIG. 4D illustrates a detail view of the proximal end of the collapsible portion of the embodiment of FIG. 4A.

The collapsible portion 41 is located distally along the speaking endotracheal tube 40, but proximal to the sealing balloon 42, as shown in FIG. 4A, such that it aligns with the vocal cords when placed into the trachea. The collapsible portion 41 is defined by a region where the main tube 44 has a gap spanned by a collapsible tube 43 where the main tube 44 terminates and restarts. FIG. 4C is a cross-sectional view (Section B) of the speaking endotracheal tube 40 at the collapsible portion 41, showing the inner tube 52, having an open inner tube lumen 52a, a balloon bridge tube 47, a suction bridge tube 48, and the collapsible tube 43. This is the breathing configuration, as shown in FIG. 4A, wherein the distal end 52b of the inner tube 52 is located distal to the collapsible portion 41 to keep the airway open across the collapsible portion 41. That is, the inner tube 52 is stiff enough to resist collapsing under the force of the vocal cords. This configuration is further illustrated in FIG. 4D, which shows a detail view (Detail A) of the proximal end of the collapsible portion 41. The proximal section 65 of the main tube 44 ends at the main tube distal end 44b. However, the inner tube 52, which is disposed within the central lumen 44a of the main tube 44, extends beyond the main tube distal end 44b, spanning across the collapsible portion 41, to provide a conduit for airflow across the collapsible region 41 in the non-speaking configuration as shown in FIGS. 4A-4D.

The balloon bridge tube 47 and the suction bridge tube 48 span the gap across the collapsible portion 41 to provide small conduits that do not collapse (at least not entirely) under the force of the vocal cords when the patient tries to speak. In the configuration shown in FIGS. 4A-4D, the collapsible region 41 is open (not collapsed) because the inner tube 52 is in place across the gap; the inner tube 52 is stiff enough to resist collapsing when the vocal cords close on the speaking endotracheal tube 40. In some embodiments, the bridge tubes 47 and 48 may be inserted into the balloon inflation lumen 45 and the suction lumen 46 respectively, as shown in FIG. 4D. The bridge tubes 47 and 48 may be press-fit, bonded, heat staked (thermal bonded), or attached in any other way known in the art. In some embodiments, the bridge tubes 47 and 48 may run part or all of the entire length inside of the main tube 44 replacing some or all of the balloon and suction lumens that normally exist in the main tube 44. The bridge tubes 47 and 48 may be made of any material and shape combination that is stiff enough to withstand the force of the vocal cords closing to maintain fluid communication with the distal end of the main tube 44; thus, in the speaking configuration, air pressure can be communicated to the balloon and suction can be applied through the suction lumen 46. For example, the bridge tubes 47 and 48 may be made of a metal such as stainless steel or a polymer, or other material, that forms a tube stiff enough to resist full collapse under the force of the vocal cords. The main tube 44 may be made of a soft polymer such as extruded PVC, or other suitable materials such as polyurethane or polyethylene.

Figure 5B:
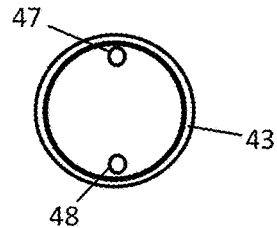
FIG. 5B illustrates a cross-sectional view through a collapsible portion of the embodiment of FIG. 5A in the open (non-speaking) state.
Figure 5C:
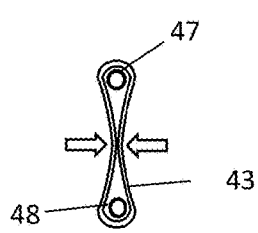
FIG. 5C illustrates a cross-sectional view through a collapsible portion of the embodiment of FIG. 5A in the closed (speaking) state.
Figure 5A:
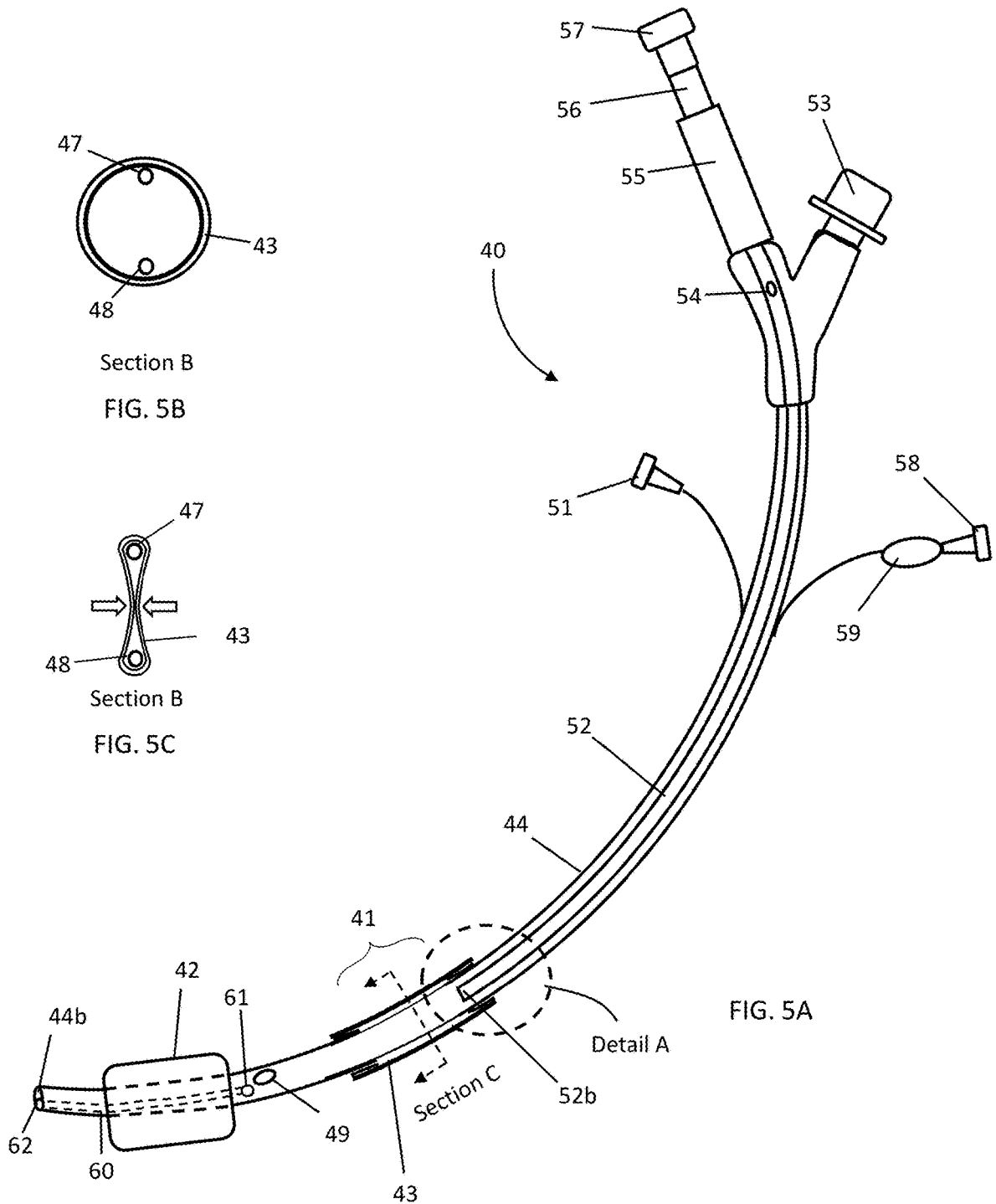
FIG. 5A illustrates a side partial cross-sectional view of an embodiment of a speaking endotracheal tube according to embodiments of the present disclosure.

Now with reference to FIG. 5A which shows a side view of the speaking endotracheal tube 40 in a speaking configuration. The inner tube 52 is retracted proximally via manipulation of the translator knob 57 on the proximal end of the speaking endotracheal tube 40. In some embodiments, the inner tube 52 may be keyed against rotation during its advancement and retraction via outer housing 55 and inner shaft 56, which are telescoping elements that may have features to prevent relative rotation such as square or off-round cross-sectional shapes. One skilled in the art would recognize that there are many methods and arrangements for slidably translating a tube within a tube, such as rotating elements that transfer rotation into translation; all of which are within the scope of this disclosure. Other examples include threaded screws and rack/pinion arrangements. Rotation of the inner tube 52 may be avoided during advancement and retraction if both inner tube 52 and main tube 44 have a defined curvature. In some embodiments, the main tube 44 may have a pre-set curvature, while the inner tube 52 is straight but flexible enough to translate through the main tube 44 without binding or substantially affecting the pre-set curvature.

After the inner tube 52 has been retracted proximally via the translator knob 57, as shown in the configuration illustrated in FIG. 5A, the distal end 52b of the inner tube 52 is located proximal to the collapsible portion 41 and therefore not supporting the collapsible portion 41. FIG. 5B is a cross-sectional view (Section C) of the speaking endotracheal tube 40 through the collapsible portion 41, showing the balloon bridge tube 47 and the suction bridge tube 48 inside of the collapsible tube 43; notably, the inner tube 52 is not present in this cross section because it is receded up the main tube 44 proximal to the collapsible portion 41.

FIG. 5C shows the cross-sectional view (Section C) of the speaking endotracheal tube 40 at the site of the collapsible portion 41 when a patient is speaking. The force of the patient's vocal cords, as indicated by block arrows, causes the collapsible tube 43 to deform. The inner diameter of the collapsible tube 43 may come into contact at opposing sides as shown, while the balloon bridge tube 47 and the suction bridge tube 48, which span the collapsible portion 41, remain open. Hence, balloon inflation and suction pressure may be maintained while the patient is speaking.

Figure 6A:
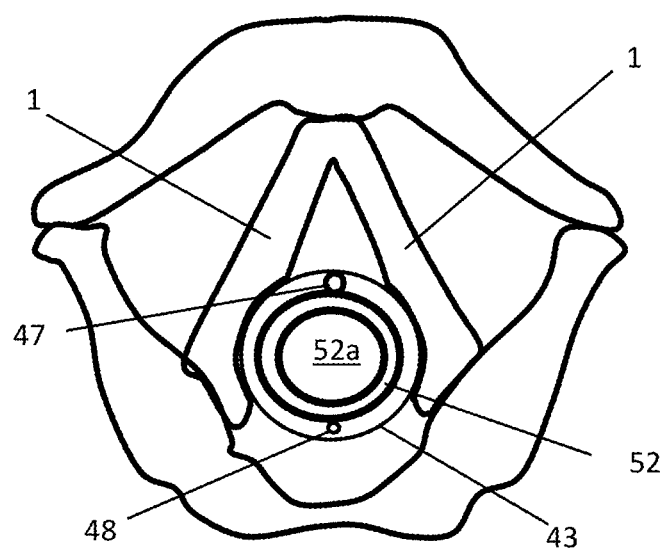
FIG. 6A illustrates a speaking endotracheal tube placed in the vocal cord anatomy while in the open (non-speaking) configuration.
Figure 6B:
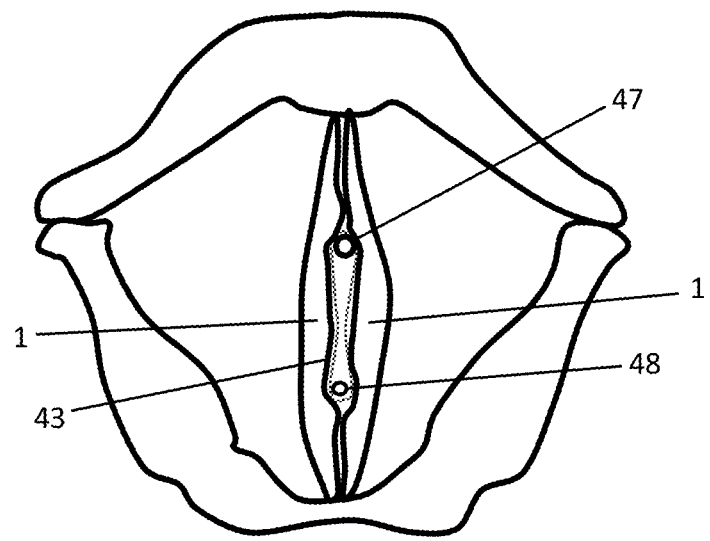
FIG. 6B illustrates a speaking endotracheal tube placed in the vocal cord anatomy while in the closed (speaking) configuration.

FIGS. 6A-6B show the speaking endotracheal tube inserted into the trachea such that the collapsible portion is aligned with the vocal cords—these views show a superior view of a transverse section at the level of the vocal cords during speaking and during normal ventilatory flow. FIG. 6A shows the vocal cords 1 maintained in an open position by the inner tube 52, which is substantially rigid enough to withstand the force of the vocal cords 1, thus preventing speech as the inner tube lumen 52a maintains an open airway. In this configuration (as in FIG. 4A) the inner tube is extended distally such that it spans the collapsible region 41. The collapsible tube 43 may deform against the inner tube 52, but for clarity it is shown spaced radially apart so that the tubes can be identified. As described above, the balloon bridge tube 47 and the suction bridge tube 48 provide fluid communication across the collapsible portion for balloon inflation and suction, respectively. In contrast, the configuration illustrated in FIG. 6B is the same superior view of a transverse section at the level of the vocal cords, but the speaking endotracheal tube 40 is in the speaking configuration; the inner tube 52 is in the retracted state to allow deformation of the collapsible tube 43 under the closing force of the vocal cords 1. The balloon bridge tube 47 and the suction bridge tube 48 are intact and provide fluid communication across the collapsible portion for balloon inflation and suction, respectively.

Figure 7A:
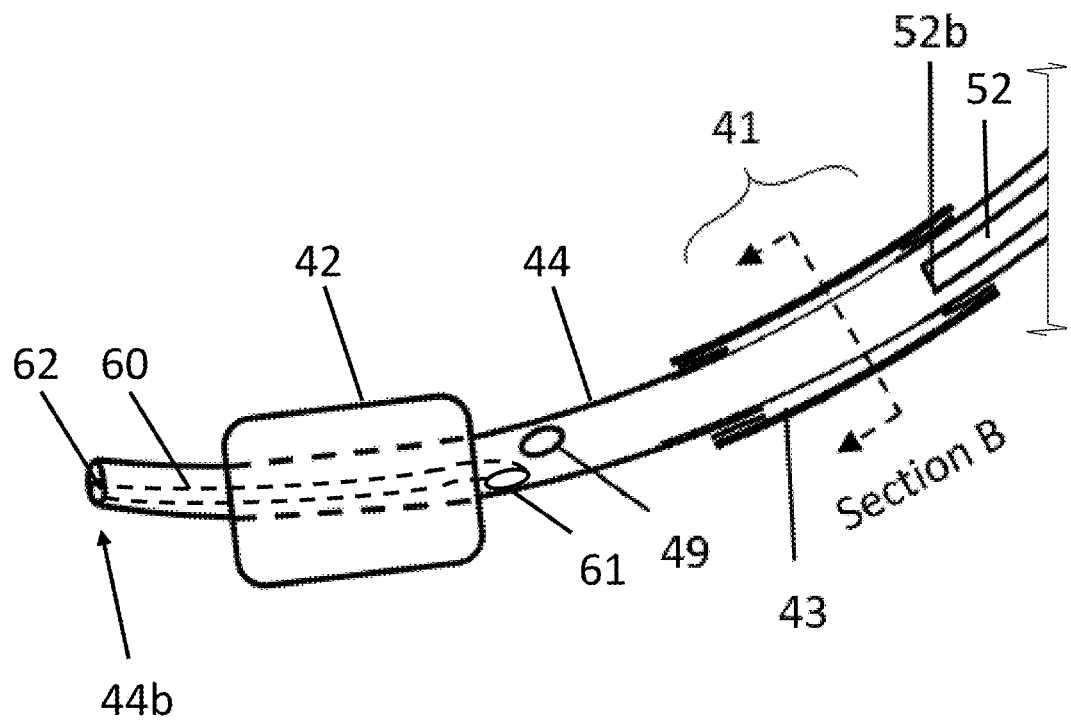
FIG. 7A illustrates the distal portion of a speaking endotracheal tube having a distal lumen that is in the open configuration.

Humans exhale when speaking, which, in combination with the vibration of the vocal cords, creates sound. When an intubated patient speaks, they need to exhale air through the vocal cords to create phonation. In order to accommodate such air flow, the speaking endotracheal tube may allow exhaled air to flow past the balloon seal while the endotracheal tube is closed off, that is, while the collapsible portion is closed due to the clamping force of the vocal cords. Conversely, when the patient is not speaking and the endotracheal tube is passing air through its lumen in a normal fashion, the flow path bypassing the balloon may not be needed, and it may be closed off. Now with reference to FIGS. 7A-7B, which show an embodiment of the distal portion of the endotracheal tube depicting a balloon bypass lumen 60 that bypasses the sealing balloon 42 in an open (FIG. 7A) and closed (FIG. 7B) configuration, respectively. The speaking configuration is shown in FIG. 7A wherein the distal end 52b, of the inner tube 52 is proximal to the collapsible portion 41. In this state, the collapsible portion 41 may be compressed, as previously shown in FIG. 5C, such that little or no air flows to the inner tube 52. The balloon bypass lumen 60 spans from the balloon bypass distal end 62 (which is at or near the main tube distal end 44b), beyond the sealing balloon 42, to a balloon bypass port 61, which may be an opening through the side of the main tube that is in fluid communication with the trachea. This arrangement allows the patient to exhale air while speaking; the air flows from the patient's lungs distal to the sealing balloon 42 to bypass the sealing balloon 42 and flows into the trachea proximal to the sealing balloon 42.

Figure 7B:
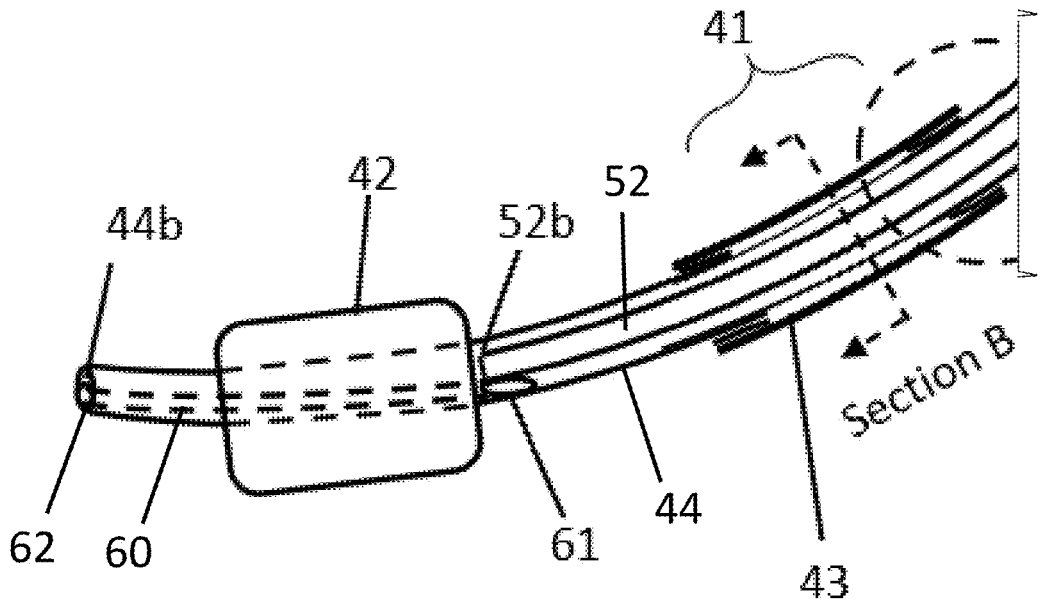
FIG. 7B illustrates the distal portion of a speaking endotracheal tube having a distal lumen that is in the closed configuration.

During normal ventilatory flow (without speaking), the balloon bypass lumen 60 is not needed, and it may be closed off. In some embodiments, the inner tube 52 may be used to close the balloon bypass lumen 60. For example, the inner tube 52 may be advanced distally beyond the collapsible portion 41 to allow normal ventilatory breathing. As illustrated in FIG. 7B, the inner tube 52 is shown advanced distally to the point where its distal end 52b (and optionally the region proximal thereof) contacts the balloon bypass lumen 60 near the balloon bypass port 61, thus closing it off by squeezing the balloon bypass lumen 60 against the main tube 44. The balloon bypass lumen 60, in the region near the balloon bypass port 61, may be offset diametrically within the main tube 44 such that it interferes with the inner tube 52 so as to deform the balloon bypass lumen 60 enough to cease expiratory flow through it. In some embodiments, the inner tube 52 may block the balloon bypass port 61, or it may pinch the balloon bypass lumen 60 distal to the balloon bypass port 61.

One skilled in the art would recognize that there are many ways to form a balloon bypass lumen within an endotracheal tube and such embodiments are within the scope of this disclosure. By way of nonlimiting example, a balloon bypass lumen may be made by coextruding it within the main tube or attaching it as a separate tube between the main tube distal end 44b and a port proximal to the balloon. Furthermore, one would also recognize that there are many approaches known in the art to actively close and open the distal lumen to air flow, all of which are within the scope of this disclosure; examples include having a valve in the lumen or the exit port, or a sliding outer sheath that can cover/uncover the port.

Figure 8:
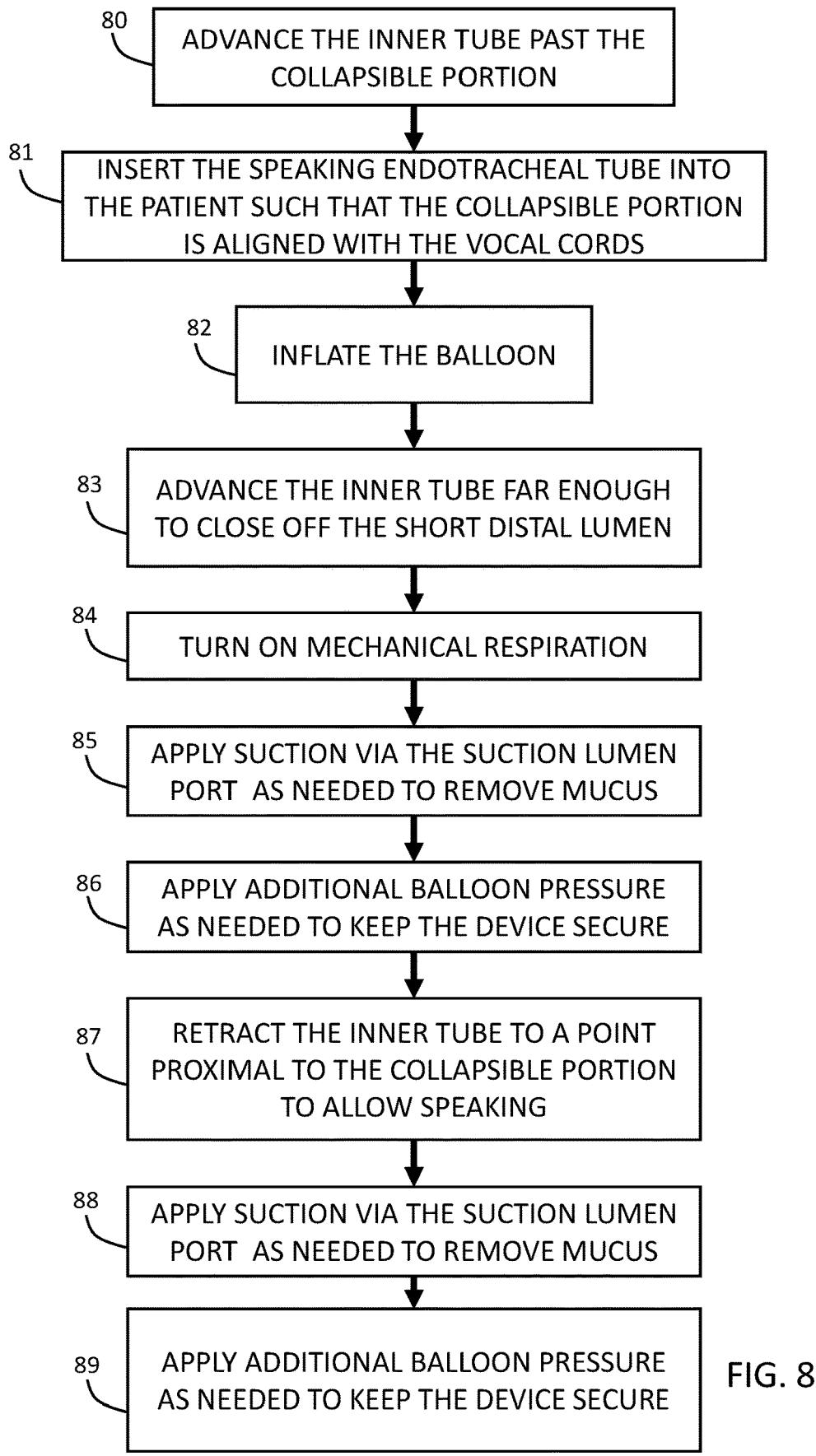
FIG. 8 illustrates a method for applying a speaking endotracheal tube to a patient according to an embodiment.

Now with reference to FIG. 8, which is a flow chart of an exemplar process for using the speaking endotracheal tube 40. While the steps are shown in an order implied by the arrows, the scope of the invention shall not be limited by this sequence, as certain steps may be rearranged or skipped altogether. Furthermore, additional steps may be added and are contemplated to be performed in the clinical setting. First, the operator may advance the inner tube 52 past the collapsible portion 41 to maintain a strong column stiffness while the device is inserted (step 80). The speaking endotracheal tube 40 may have markings or tactile feedback (e.g., detent) or any other method known in the art to convey the position of the inner tube 52 (relative to the main tube 44) to the operator; i.e., breathing position or respirator position. The operator inserts the speaking endotracheal tube 40 into the trachea to the point where the collapsible portion 41 is aligned with the vocal cords 1 (step 81). The speaking endotracheal tube 40 may have markings to convey the position (e.g., depth in the body) of the speaking endotracheal tube 40 to the operator. The operator inflates the sealing balloon 42 via the pressure connector 58 (step 82). The inner tube 52 may be advanced distally into further to close off the balloon bypass lumen 60 if it has not already been fully advanced (step 83). Mechanical respiration may be turned on to enable respiratory flow (step 84). As needed, during ventilation, suction may be applied via the suction connector 51 to evacuate mucus or other matter from the trachea proximal to the sealing balloon 42 (step 85). In addition, pressure may be applied via the pressure connector 50 to further inflate the sealing balloon 42 (step 86). To allow the patient to speak, the inner tube 52 is retracted proximally beyond the collapsible portion 41 (step 87). Similar to the breathing configuration, in the speaking configuration, suction and pressure may be applied via the suction connector 51 and the pressure connector 50 (steps 88 and 89). After the patient finishes speaking, the inner tube 52 may be advanced distally to resume normal respiratory flow. The patient will be able to close the collapsible section and speak with the ventilator running because normal ventilation pressures are low, ranging from approximately 14-18 cm H2O, while the maximum expiratory pressure in males is on the order of 233+/−84 cm H2O.

While this invention has been particularly shown and described with references to example embodiments thereof, it will be understood by those skilled in the art that various changes in form and details may be made therein without departing from the scope of the invention(s) encompassed by the appended claims. While the above is a complete description of the certain embodiments of the invention, various alternatives, modifications, and equivalents may be used. The various devices and method steps of the embodiments disclosed herein may be combined or substituted with one another, and such alternative embodiments fall within the scope of the claimed invention(s). Therefore, the above description should not be taken as limiting in scope of the invention(a) which is defined by the appended claims.

What is claimed is:

1. An endotracheal tube system comprising:
   an elongate tube comprising:
   a central lumen;
   a suction lumen;
   a balloon inflation lumen, and
   a collapsible section disposed toward a distal end of the elongate tube that is capable of substantially flattening under the force of vocal cords; and
   a balloon disposed on the elongate tube distal to the collapsible section and in fluid communication with the balloon inflation lumen,
   a balloon bypass lumen capable of providing fluid communication between a portion of a trachea distal to the balloon and a portion of the trachea proximal to the balloon,
   wherein the balloon bypass lumen comprises an outlet proximal to the balloon that is capable of being closed when a patient is not speaking, and
   an inner tube slidably disposed inside of the central lumen, wherein the inner tube is capable of blocking the balloon bypass lumen to prevent air flow through the balloon bypass lumen.

2. The endotracheal tube system of claim 1 wherein the collapsible section comprises:
   a flexible tube attached to a proximal section of the elongate tube and to a distal section of the elongate tube.

3. The endotracheal tube system of claim 1 wherein the collapsible section comprises at least one substantially non-collapsible tube for providing fluid communication across the collapsible section.

4. The endotracheal tube system of claim 1 wherein the inner tube has a radial stiffness sufficient to resist collapsing due to the force of the vocal cords.

5. A speaking endotracheal tube comprising:
   a tubular body configured to be placed in a trachea of a patient; and
   an inner tube slidably located in a lumen of the tubular body, the inner tube capable of transmitting air between the trachea and a ventilator fitting on the speaking endotracheal tube;
   further comprising a balloon and a balloon bypass lumen, the balloon bypass lumen providing fluid communication between a portion of the trachea distal to the balloon and a portion of the trachea proximal to the balloon;
   wherein the balloon bypass lumen comprises an outlet proximal to the balloon that is capable of being closed when the patient is not speaking.

6. The speaking endotracheal tube of claim 5 wherein the inner tube comprises an aperture near its proximal end for transmitting air between its lumen and the lumen of the tubular body.

7. The speaking endotracheal tube of claim 5 wherein the tubular body comprises a collapsible section configured to align with the patient's vocal cords.

8. The speaking endotracheal tube of claim 7 wherein the collapsible section comprises at least one substantially non-collapsible tube for providing fluid communication across the collapsible section.

9. The speaking endotracheal tube of claim 8 wherein the at least one substantially non-collapsible tube is in fluid communication with one of a suction lumen or a balloon inflation lumen.

10. The speaking endotracheal tube of claim 8 wherein the inner tube is capable of blocking the balloon bypass lumen to prevent air flow through the balloon bypass lumen.

11. A method of operation for inserting a speaking endotracheal tube into a patient, wherein:
the speaking endotracheal tube comprises:
an elongate tube comprising:
a central lumen;
a suction lumen;
a balloon inflation lumen, and
a collapsible section;
an inner tube slidably disposed in a lumen of the elongate tube; and
a balloon disposed on the elongate tube distal to the collapsible section and in fluid communication with the balloon inflation lumen, the method comprising:
placing the speaking endotracheal tube into the trachea of the patient;
wherein the elongate tube further comprises a balloon bypass lumen providing fluid communication between a portion of the trachea distal to the balloon and a portion of the trachea proximal to the balloon;
further comprising the step of moving the inner tube within the elongate tube such that the inner tube blocks fluid communication of the balloon bypass lumen.

12. The method of claim 11 further comprising aligning the collapsible section with the vocal cords of the patient and inflating the balloon to secure the speaking endotracheal tube.

13. The method of claim 12 further comprising moving a distal end of the inner tube to a position proximal to the collapsible section to allow speaking.

14. The method of claim 12 further comprising moving the inner tube such that its distal end resides distal to the collapsible section so that the inner tube extends beyond the vocal cords.

* * * * *